United States Patent [19]

Gay

[11] 4,138,438

[45] Feb. 6, 1979

[54] PROCESS FOR PRODUCING PENTACHLORONITROBENZENE

[75] Inventor: Walter A. Gay, Cheshire, Conn.

[73] Assignee: Olin Corporation, New Haven, Conn.

[21] Appl. No.: 826,603

[22] Filed: Aug. 22, 1977

[51] Int. Cl.² .............................................. C07C 79/12
[52] U.S. Cl. ................................................. 260/646
[58] Field of Search .................. 260/646; 423/386, 398

[56] References Cited

U.S. PATENT DOCUMENTS 4,026,955  5/1977  Breaux et al. ........................ 252/646
4,044,111  8/1977  Furuta et al. ........................ 423/386

*Primary Examiner*—Benjamin R. Padgett
*Assistant Examiner*—Deborah L. Kyle
*Attorney, Agent, or Firm*—William A. Simons; Thomas P. O'Day

[57] ABSTRACT

An improvement is disclosed in the preparation of pentachloronitrobenzene by the reaction of pentachlorobenzene with mixed nitration acid. The improvement, which is aimed at reducing undesirable impurities in the product, includes the use of a selected process step, wherein excess, unreacted nitric acid is reacted with HCl.

11 Claims, No Drawings

PROCESS FOR PRODUCING PENTACHLORONITROBENZENE

BACKGROUND OF THE INVENTION

1. Field of the Invention

This invention relates to a process for producing pentachloronitrobenzene by the nitration of pentachlorobenzene.

2. Description of the Prior Art

Pentachloronitrobenzene (sometimes referred to herein as PCNB) is widely used today as a soil fungicide. It is particularly effective in controlling plant diseases caused by botrytis, fusarium, rhizoctonia and anthracnose. However, some commercial products of PCNB have been questioned on environmental grounds because of the presence of relatively large amounts of two contaminants contained therein. These chemicals, pentachlorobenzene (sometimes referred to herein as PENTA) and hexachlorobenzene (sometimes referred to herein as HCB), have been found to bioaccumulate in the fatty tissue of animals. Therefore, their presence in this desirable soil fungicide may cause a health hazard. For example, foodstuffs produced from soil which has been treated with quantities of impure fungicide may have PENTA and HCB leached into them and, thus, these impurities may accumulate in humans when they are later eaten. Also, cattle and other livestock that graze on treated grass or other pastures or grains may accumulate undesirable amounts of these impurities. And, furthermore, the farmer, when applying PCNB to soil, may breathe in significant quantities of these impurities.

Several methods are now known for the preparation of PCNB. Those of significance to the process described herein involve the nitration of pentachlorobenzene with mixed nitration acid, which, as used in the specification and claims herein, consists essentially of a mixture of nitric and sulfuric acids.

In particular, U.S. Pat. No. 4,026,955, issued on May 31, 1977 to Breaux, Newman and Quinnett, teaches one such process. In this patent, it is disclosed that PCNB having reduced HCB content can be produced by a process wherein, first, pentachlorobenzene and mixed nitration acid are mixed together at an initial reaction temperature in the range of 100°–120° C. This resulting reaction mixture is then heated to an intermediate temperature in the range from 130° C. up to the melting point of PCNB and this reaction temperature is maintained for a time period sufficient to deplete the nitric acid concentration to a value of not more than 1% by weight of the reaction mixture. And, then, this reaction mixture is heated to a temperature in the range of 142° C. to 160° C. to form a melt and, finally, this melt is cooled to recrystallize the PCNB product.

While the process disclosed in this patent represents a significant advance in producing relatively high purity PCNB, more recent research has shown that HCB impurity level can be further substantially lowered by the process of the present invention.

BRIEF SUMMARY OF THE INVENTION

The present invention is directed to a process for producing pentachloronitrobenzene wherein (a) pentachlorobenzene and a mixed nitration acid consisting essentially of sulfuric acid and nitric acid are mixed together at a temperature in the range from about 100° C. to about 120° C., the nitric acid being in a molar excess over the stoichiometric amount required to react with the pentachlorobenzene;

(b) the resulting reaction mixture is then heated to a temperature in the range of about 130° C. to about 140° C. and the reaction mixture is maintained within this temperature range for a period of time which is no longer than is necessary for the conversion of pentachlorobenzene to pentachloronitrobenzene to be substantially complete;

(c) substantially all of the remaining nitric acid in the reaction mixture is reacted with HCl;

(d) the resulting reaction mixture is then heated to a temperature in the range of about 142° C. to about 160° C. to form a melt of pentachloronitrobenzene; and (e) the reaction mixture is then cooled to recrystallize the melted pentachloronitrobenzene contained therein.

DETAILED DESCRIPTION

The process of the present invention is an improvement upon the process for producing PCNB disclosed in the above-cited U.S. Pat. No. 4,026,955, which is incorporated by reference herein in its entirety. As discussed above, that patent described a process for producing a highly pure PCNB product by reacting PENTA with a mixed nitration acid, wherein several reaction stages of differing temperatures were utilized. Also, as mentioned in that patent, it was found that the formation of the HCB impurity was a temperature-related phenomenon and a dramatic increase in HCB formation occurs in a mixed acid system at or above temperatures of 138°–142° C. Furthermore, that patent stated that when nitric acid concentration was depleted to a value of 1% by weight or less of the liquid fraction of the slurry prior to raising the temperature above the melting point of PCNB, the rate of hexachlorobenzene formation during the subsequent melting step undergoes a dramatic decrease. However, while it was originally thought that the formation of HCB in this patented process was at a desirable level, more recent research has found that the amount of HCB can be even further lowered in the final PCNB product. Specifically, it has now been found that the presence of any excess nitric acid (e.g., amounts even less than 1% by weight of the reaction mixture) can cause formation of some hexachlorobenzene impurity at the reaction temperatures employed herein. Accordingly, the present process presents a method both for controlling or minimizing the hexachlorobenzene formation in the heating step at 130°–140° C. and preventing the formation of substantially any amounts of this impurity in the subsequent melting step at 142°–160° C.

The pentachlorobenzene (PENTA) employed herein as a reactant can be obtained from any conventionally available source. For example, it may be prepared commercially by chlorinating benzene, mono-, di-, tri-, or tetrachlorobenzene or mixtures of any of these and then subjecting the resulting reaction mixture to any conventional recovery means, for example, distillation, in order to recover the pentachlorobenzene. The purity of the pentachlorobenzene is not a critical factor of the present process. However, it is preferred that the pentachlorobenzene be as pure as possible. It is important that it be substantially free of hexachlorobenzene so that the present process will not pass along appreciable amounts of this impurity to the PCNB.

The mixed nitration acid employed herein, as indicated above, consists essentially of sulfuric and nitric acids. However, very small amounts of impurities such as sulfur trioxide (as in commercial oleum) and water may be present, if desired. The percentages of nitric and sulfuric acids in this mixed nitration acid are not critical to the present invention. However, preferably, it is advantageous to use a mixed nitration acid having a nitric acid content of from about 10% to about 25%, more preferably from about 15% to 20%, by weight to assure the presence of sufficient sulfuric acid which acts simultaneously as a solvent and catalyst and also serves to take up any water formed during the reaction. In particular, regard to its catalytic effect, it is known that the presence of sulfuric acid protonates the nitric acid and, thus, makes the nitric acid a more reactive species for the present invention.

Sufficient mixed nitration acid should be utilized to provide a molar excess of nitric acid over the pentachlorobenzene. This molar excess will ensure substantially complete conversion (usually at least about 98% by weight) of the pentachlorobenzene. Besides, at the reaction temperatures employed herein, minor amounts of the nitric acid may be decomposed into volatile gases and thereby be unavailable for reaction. So preferably, at least about 25% molar excess of nitric acid should usually be employed to assure consistently high conversion of the pentachlorobenzene. More preferably, from about 40% to about 100%, most preferably 50–75%, molar excess of nitric acid over pentachlorobenzene may be utilized. Thus, sufficient mixed nitration acid may be preferably utilized to provide at least about 1.25, more preferably about 1.4–2.0, most preferably about 1.5–1.75, moles of nitric acid per mole of pentachlorobenzene.

The initial step of the present process is mixing together pentachlorobenzene and the mixed nitration acid at a reaction temperature from about 100° C. to about 120° C. This initial reaction temperature range is critical to the present invention. At mixing temperatures below about 100° C., production problems such as slow conversion of the pentachlorobenzene, difficult temperature control and excess viscosity may be expected to be encountered. Moreover, at initial reaction temperatures above about 120° C., the formation of relatively substantial amounts of hexachlorobenzene occurs so that the resulting pentachloronitrobenzene product may be unacceptable because of undesirably high levels of hexachlorobenzene contained therein. Accordingly, it is necessary to conduct the addition or mixing of these two reactants within the range of about 100° C. to about 120° C. Preferably, the addition of these two reactants is carried out in the range of about 105° C. to about 115° C. Moreover, the pentachlorobenzene may be added to the mixed acid or vice versa as long as their proper temperature control is maintained.

During this mixing step, the reaction of pentachlorobenzene with nitric acid to form PCNB occurs almost simultaneously with their addition together. The pentachloronitrobenzene formed by this reaction is a solid which normally falls to the bottom of the reaction mixture at the later stages of this first step. In this initial reaction step, it is believed 85–98% by weight of the pentachlorobenzene is converted. However, it is further believed that a small percentage (estimated to be from about 2.0% to about 0.5% by weight of the original amount) of the pentachlorobenzene (along with some sulfuric acid) is occluded or entrapped within the solid pentachloronitrobenzene product. This entrapped pentachlorobenzene impurity is unable to react with the nitric acid and, thus, may remain as an undesirably high level impurity in the final pentachloronitrobenzene product unless the subsequent heating step of the present process is employed. It has also been found that hexachlorobenzene is not formed to any significant degree during this early low temperature stage of the reaction.

The reaction of pentachlorobenzene with nitric acid is highly exothermic. In order to control the temperature of the reaction mixture during addition, it is necessary to add the two reactants together at a rate sufficient to maintain the temperature to within the above-stated initial temperature range. Normally, the addition step may generally take from about one to about five hours. Furthermore, external cooling may be provided for more rapid addition, but such cooling is ordinarily not necessary. Also, it may be desirable to employ known stirring or agitating means to keep the reactants well mixed and to also maintain proper temperature control.

After the addition or mixing of reactants at about 100°–120° C. is completed, the reaction mixture is heated to about 130° C. to about 140° C. and maintained in this temperature range for a period of time which is not greater than the time necessary for the conversion of pentachlorobenzene to pentachloronitrobenzene to be substantially completed (i.e., at least about 98% by weight of PENTA is converted to PCNB). Preferably, the reaction mixture is heated to about 133°–138° C.

This heating step is necessary to the present process because the solid pentachloronitrobenzene product formed in the prior mixing step will undergo partial melting and/or changes in crystal structure at these temperatures of about 130°–140° C. These physical changes, coupled with the increased reaction temperature, will cause the unreacted pentachlorobenzene entrapped in the solid pentachloronitrobenzene product to react with the nitric acid. Accordingly, the pentachlorobenzene that was not reacted in the mixing step is now substantially converted to pentachloronitrobenzene by this step. Further, the final PCNB product will, thus, contain a minimum amount of the undesirable PENTA.

The maximum duration limit of this step is also an important feature of the present process. It has been found that hexachlorobenzene formation increases steadily with the passage of time at the reaction temperatures of this step, namely, about 130°–140° C. However, as explained above, this heating step must be maintained for a sufficient period of time in order to partially melt the solid PCNB product and thereby allow the exposed PENTA to react with nitric acid. Therefore, some hexachlorobenzene, in any event, will be formed during this step. But, it is desirable to terminate this step as soon as possible so as to keep the formation of HCB to a minimum. Accordingly, it is an important feature of the present process not to allow this heating step to proceed for any longer period of time than is necessary for the conversion of PENTA to PCNB to be substantially complete. Allowing this heating step to be maintained any longer only causes the formation of HCB without any appreciable benefit to the process. A definite time period in minutes or hours cannot be generally given because this may vary with the types of equipment and/or procedures (e.g., heating with or without pressure) which may be utilized for carrying out this heating step on a commercial scale. However, this heating step is normally no more than about one hour long. The ratio of time to the conversion of PENTA to PCNB may be determined by simple experimentation whereby various samples are taken at various times after the beginning of this heating step and these samples are analyzed for the percentage of PENTA left unconverted. This step should be over before the percentage of PENTA remains unchanged for any appreciable length of time. Preferably, this heating step is held for a sufficient period of time which results in substantially complete conversion of PENTA to PCNB.

Furthermore, in a preferred embodiment of the present invention, the reaction time above about 130° C. can be minimized further by utilizing a two-stage heating step after the mixing step at 100°-120° C. In particular, this two-stage heating step is carried out by first heating to and maintaining the reaction mixture at a temperature within the range of about 121° C. to about 129° C., more preferably about 123°-127° C. Next, the reaction mixture is reheated to about 130°-140° C. and maintained at that range for a period of time no longer than is necessary to have substantially complete conversion of the pentachlorobenzene to pentachloronitrobenzene. The heating step at this lower temperature range of about 121°-129° C. will cause further conversion of the unreacted PENTA to PCNB. Thus, the amount of unconverted PENTA left in the reaction mixture after this heating at about 121°-129° C. will be less than if the reaction mixture is directly heated to about 130°-140° C. Moreover, the time for substantially complete conversion of PENTA to PCNB at this latter temperature range will be shorter, thereby minimizing the possibility of HCB formation in the reaction mixture. A purer PCNB product therefore may result.

After this heating step at about 130°-140° C., substantially all of the excess nitric acid still present in the reaction mixture is reacted with HCl. Normally, a sufficient quantity of HCl is simply added to the reaction mixture. However, HCl may alternatively be generated in situ by adding a chlorine-containing salt such as sodium chloride to the reaction mixture. The chlorine-containing salt will be converted to HCl through a reaction with the $H_2SO_4$. The resulting HCl may then react with excess nitric acid in the reaction mixture. Therefore, the term "HCl" as employed in the specification and claims herein encompasses any and all means by which it is provided, including direct addition or in situ formation.

The reactions believed to be caused by the addition of HCl and its in situ generation in the reaction mixture are illustrated by equations (1), (2A) and (2B), respectively:

$$2HNO_3 + 4HCl \rightarrow N_2O_3 + 2Cl_2 + 3H_2O \quad (1)$$

$$4NaCl + 2H_2SO_4 \rightarrow 2Na_2SO_4 + 4HCl \quad (2A)$$

$$2HNO_3 + 4HCl \rightarrow N_2O_3 + 2Cl_2 + 3H_2O \quad (2B)$$

Further, the volatile gases $N_2O_3$ and $Cl_2$ may interact to form other volatile gases NOCl and $NO_2$ according to the reaction indicated by equation (3):

$$2N_2O_3 + Cl_2 \rightarrow 2NOCl + 2NO_2 \quad (3)$$

The destruction of the excess nitric acid with HCl has two beneficial effects on the present process. The first one is prevention of substantially any HCB formation in the subsequent melting step, as discussed below. The second is that the destruction of the nitric acid into volatile gases such as $N_2O_3$ and $Cl_2$ aids in the subsequent clean-up of spent sulfuric acid and reduces recovery costs.

The amount of HCl added to the reaction mixture should be sufficient to react with substantially all of the nitric acid present therein, as shown in equations (1), (2A) and (2B). However, it should be noted that since most of the nitric acid has already been converted by reaction with the PENTA, only relatively small amounts of nitric acid are usually left in the reaction mixture. Thus, only relatively small amounts of HCl (e.g., 0.25-1.0 mole per mole of PCNB being formed) are needed for reaction with the excess nitric acid.

Other reducing agents of nitric acid besides HCl have been considered. For example, cupric sulfide, ferrous sulfate and oxalic acid have been employed but were found to give poor results. Furthermore, reducing agents such as sodium hydrosulfite, sodium thiosulfate and sodium hydrosulfide were found to give some acceptable destruction of excess nitric acid. However, these reducing agents have certain disadvantages associated with them. These disadvantages include the formation of malodorous gases, highly exothermic reactions and precipitation of free sulfur. The use of HCl, on the other hand, gave slightly endothermic reactions, produced easily workable products with nitric acid and is a readily available chemical.

Following the reaction of the nitric acid with HCl, the reaction mixture is then heated to a temperature in the range of about 142° C. to about 160° C. This further heating step is necessary to completely melt the solid PCNB product formed in both the prior mixing and heating steps. This melt formation is desired in order to recover larger crystals of PCNB and to allow entrapped $H_2SO_4$ and other contaminants to escape from the solid product. Preferably, temperatures in the range of about 145° C. to about 155° C. are utilized.

The time duration for this melting step is not critical to the present process. The desired time could certainly vary and one having ordinary skill in the art could easily select the most appropriate time for each situation. The duration of this step has no effect on the formation of HCB. It has been found that by virtue of the destruction of substantially all of the nitric acid no substantial increase in HCB content in this melting step results, regardless of the duration of this step. This is a significant advantage over the process disclosed in U.S. Pat. No. 4,026,955. In a preferred embodiment of the present invention, the time duration of this step is normally not much more than what is required to produce a complete melt of the PCNB product, approximately 0.25 to 1.0 hour.

After formation of this melt, the reaction mixture is cooled to recrystallize the PCNB contained in the reaction mixture. This cooling may be done by any conventional means such as by removing the heat source or employing the cooling jacket around the reaction mixture. Normally, dropping the temperature of the reaction mixture below about 100° C., preferably from about 20°-80° C., for a sufficient amount of time will result in recrystallization of PCNB product in excess of 95% by weight yields.

After the cooling step is completed, the solid pentachloronitrobenzene crystals in the reaction mixture may be recovered or subjected to further chemical reaction in the production of other chemicals. Product recovery can be achieved by any suitable technique such as any conventional liquid-solid separation means such as filtrating, centrifuging, decanting and the like. Preferably, the solid crystal and the pentachloronitrobenzene product were recovered by filtering, followed by washing with a suitable solvent such as water to remove residuals. The recovered pentachlorobenzene is a highly pure product. Each of the levels of hexachlorobenzene and pentachlorobenzene is preferably less than 0.6%, more preferably less than 0.3%, by weight of the total pentachloronitrobenzene product.

The following examples and comparisons further illustrate the present invention. All parts and percentages are by weight unless otherwise expressly indicated.

EXAMPLE 1

Into a three-neck 300 ml flask equipped with a mechanical agitator, thermometer and condenser was charged 50 g of 99.7% pure powdered pentachlorobenzene which was heated to 105°–110° C. by means of an oil bath. The flask was then charged with 113 g of mixed nitric acid which contained 16.5% by weight nitric acid and 83.5% by weight sulfuric acid. This mixed nitric acid was gradually added over a period of three hours while the reaction mixture was stirred. Following this addition, the reaction mixture was heated to 125° C. for one hour, followed by further heating at 140° C. for one hour. Then, 7 g of HCl was gradually added over a time period of 15 minutes. After said HCl addition, the reaction mixture was heated again to raise the reaction temperature to 145° C. and to form a liquid melt of pentachloronitrobenzene. The reaction mixture was maintained at this temperature for 15 minutes. Next, the reaction mixture was cooled to 30°–70° C. by removal of the oil bath and by blowing cool air on the flask for about 15 minutes. The reaction mixture was then filtered by suction. The pentachloronitrobenzene product in the filter cake was pressed dry and washed twice with 100 ml water each time. After drying at reduced pressure (20 tor), the product was analyzed by Vapor Phase Chromatography (VPC). In this specific example, the product was of exceptional quality with an assay of 99.20% pentachloronitrobenzene, 0.05% pentachlorobenzene and 0.37% hexachlorobenzene.

EXAMPLE 2

The experiment of Example 1 was repeated except that the reaction mixture was further heated at 135° C. for one hour instead of 140° C. The resulting product assay was 99.13% pentachloronitrobenzene, 0.26% pentachlorobenzene and 0.24% hexachlorobenzene.

EXAMPLE 3

The experiment of Example 1 was repeated except that the reaction mixture was further heated at 130° C. for one hour instead of 140° C. The resulting product assay was 99.10% pentachloronitrobenzene, 0.53% pentachlorobenzene and 0.22% hexachlorobenzene.

EXAMPLE 4

The experiment of Example 1 was repeated except that the reaction mixture was not heated to 125° C. for one hour, followed by further heating at 140° C. for one hour. Instead, the reaction mixture was simply heated for one hour at 135° C. The resulting product assay was 99.24% pentachloronitrobenzene, 0.15% pentachlorobenzene and 0.40% hexachlorobenzene.

EXAMPLE 5

The experiment of Example 1 was repeated except that the reaction mixture was not heated to 125° C. for one hour, followed by further heating at 140° C. for one hour. Instead, the reaction mixture was simply heated for one hour at 130° C. The resulting product assay was 98.38% pentachloronitrobenzene, 1.17% pentachlorobenzene and 0.27% hexachlorobenzene.

Comparisons 1–5

The experiments of Examples 1–5 were repeated except that HCl was not added prior to the melting step. The resulting product assay are shown in Table I below. Comparing each corresponding example and comparison illustrates a decrease in the percent of HCB when the HCl addition is employed.

TABLE I

| Comparison | Addition (Hr.) at 105–110° C | Post Reaction (Hr.) at 125° C | 130° C | 135° C | 140° C | Product Assay % By Weight PCNB | PENTA | HCB |
|---|---|---|---|---|---|---|---|---|
| 1 | 3 | 1 hr. | — | — | 1 hr. | 99.10 | 0.08 | 0.48 |
| 2 | 3 | 1 hr. | — | 1 hr. | — | 99.17 | 0.24 | 0.47 |
| 3 | 3 | 1 hr. | 1 hr. | — | — | 98.10 | 0.94 | 0.73 |
| 4 | 3 | — | — | 1 hr. | — | 98.92 | 0.04 | 0.78 |
| 5 | 3 | — | 1 hr. | — | — | 99.10 | 0.06 | 0.51 |

What is claimed is:

1. A process for producing pentachloronitrobenzene comprising
   (a) mixing together pentachlorobenzene and a mixed nitration acid consisting essentially of sulfuric acid and nitric acid at a temperature in the range from about 100° C. to about 120° C., said nitric acid being in molar excess of said pentachlorobenzene;
   (b) heating the resulting reaction mixture to a temperature in the range of about 130° C. to about 140° C. and maintaining said reaction mixture within this temperature range for a period of time which is no longer than is necessary for the conversion of pentachlorobenzene to pentachloronitrobenzene to be substantially complete;
   (c) reacting substantially all of the remaining nitric acid in said reaction mixture with HCl;
   (d) heating said reaction mixture to a temperature in the range of about 142° C. to about 160° C. to form a melt of pentachloronitrobenzene; and
   (e) cooling said reaction mixture to recrystallize the melted pentachloronitrobenzene.

2. The process of claim 1 wherein said reaction mixture is maintained at a temperature in the range of about 121° C. to about 129° C. after step (a) and before step (b).

3. The process of claim 1 wherein said mixed nitration acid has a nitric acid content of from about 10% to about 25% by weight.

4. The process of claim 1 wherein said heating step (b) is maintained for a sufficient amount of time in order to obtain substantially complete conversion of pentachlorobenzene to pentachloronitrobenzene.

5. The process of claim 1 wherein said nitric acid is utilized in at least about 25% molar excess over said pentachlorobenzene.

6. The process of claim 5 wherein HCl is added to said reaction mixture.

7. The process of claim 6 wherein said mixed nitration acid has a nitric acid content of from about 10% to about 25% by weight.

8. The process of claim 7 wherein said reaction mixture is maintained at a temperature in the range of about 121° C. to about 129° C. after step (a) and before step (b).

9. The process of claim 8 wherein said heating step (b) is maintained for a sufficient amount of time in order to obtain substantially complete conversion of pentachlorobenzene to pentachloronitrobenzene.

10. The process of claim 9 wherein said heating step (b) is carried out at a temperature in the range from about 133° C. to about 138° C.

11. The process of claim 10 wherein said mixing step (a) is carried out at a temperature in the range of about 105° C. to about 115° C.

* * * * *